US009243287B2

(12) United States Patent
Brennan et al.

(10) Patent No.: US 9,243,287 B2
(45) Date of Patent: Jan. 26, 2016

(54) ENDPOINT TAQMAN METHODS FOR DETERMINING ZYGOSITY OF COTTON COMPRISING CRY1AC EVENT 3006-210-23

(75) Inventors: Carolyn Brennan, Zionsville, IN (US); Wesley A. Marchione, Greenfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 1069 days.

(21) Appl. No.: 13/267,692

(22) Filed: Oct. 6, 2011

(65) Prior Publication Data
US 2012/0115142 A1 May 10, 2012

Related U.S. Application Data

(60) Provisional application No. 61/390,860, filed on Oct. 7, 2010.

(51) Int. Cl.
C12P 19/34 (2006.01)
C12Q 1/68 (2006.01)

(52) U.S. Cl.
CPC ........ *C12Q 1/6851* (2013.01); *C12Q 2561/101* (2013.01)

(58) Field of Classification Search
None
See application file for complete search history.

(56) References Cited

U.S. PATENT DOCUMENTS

| 7,179,965 | B2 * | 2/2007 | Song et al. ............ 800/302 |
| 7,786,353 | B2 | 8/2010 | Fernandes |
| 2005/0216969 | A1 | 9/2005 | Song et al. |
| 2006/0057564 | A1 | 3/2006 | Wang et al. |

OTHER PUBLICATIONS

Marras et al. (2002) Nucl. Acids Res. vol. 30 No. 21 e 122.*
Aguilera et al. (2008) Food Anal. Methods. DOI 10.1007/s1261-008-9036-1.*
Lee et al. (2007) Annals of Botany 100:1391-1401 (doi: 10.1093/aob/mcm232, available on line at www.aob.oxfordjournals.org.*
Biorad. Real-Time PCR Applications Guide. 2006 [retrieved Jan. 18, 2012]. Available on the internet: <URL: http://www.gene-quantification.de/real-time-per-guide-bio-rad.pdf>. Especially p. 24 table 2.1; 105 pages.
Liu et al. An Accurate and Rapid PCR—Based Zygosity Testing Method for Genetically Modified Maize, Molecular Plant Breeding. GMO Safety Research May 28, 2010 vol. 1 No. 1 pp. 1-4. Especially p. 3 table 1, abstract; 5 pages.
Yi et al. Quantitative real-time PCR assay to detect transgene copy number in cotton (Gossypium hirsutum). Anal Biochem Apr. 1, 2008 vol. 375 No. 1 pp. 150-152. Especially abstract.; 4 pages.

* cited by examiner

*Primary Examiner* — Suchira Pande
(74) *Attorney, Agent, or Firm* — Ronald S. Maciak; Faegre Baker Daniels LLP

(57) ABSTRACT

A method for zygosity analysis of the cotton Cry1Ac event 3006-210-23 is provided. The method provides 3006-210-23 event-specific and cotton-genome-specific primers and TaqMan probe combinations for use in an endpoint biplex TaqMan PCR assay capable of determining event zygosity and for assisting in event introgression and breeding.

10 Claims, 4 Drawing Sheets

ENDPOINT TAQMAN METHODS FOR DETERMINING ZYGOSITY OF COTTON COMPRISING CRY1AC EVENT 3006-210-23

CROSS REFERENCE TO RELATED APPLICATIONS

This application claims priority to U.S. Provisional Patent Application Ser. No. 61/390,860, filed Oct. 7, 2010, the entire disclosure of which is expressly incorporated herein by reference.

BACKGROUND OF THE INVENTION

WIDESTRIKE is a commercial cotton product comprising two synthetic *Bacillus thuringiensis* gene events: a cry1Ac-based event 3006-210-23 and a cry1F-based event 281-24-236, which together provide broad spectrum resistance to insect attack. The events are discussed in more detail in, for example, U.S. Pat. No. 7,179,965.

Cotton is an allotetraploid species which contains one A-subgenome and one D-subgenome per haploid chromosome. Transgenic WIDESTRIKE cotton plants contain a single copy event of the transgene insert in only one of the two subgenomes. Since the two subgenomes have high similarity in nucleotide sequences, oligonucleotide primers and probes specific for the null allele (designed from the flanking region of the transgene inserted into one subgenome) often amplify the fragment in the other subgenome. As such, it can be difficult to differentiate wild-type samples from plant samples that contain the transgene.

Various methods can be used to detect the presence of a given event in a sample. One example is the Pyrosequencing technique as described by Winge (Innov. Pharma. T ech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene insert/flanking sequence due to successful amplification, hybridization, and single or multi-base extension. (This technique is usually used for initial sequencing, not for detection of a specific gene when it is known.)

Fluorescence Polarization is another method that can be used to detect an amplicon. Following this method, an oligonucleotide is designed to overlap the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

The Invader assay (Third Wave Technologies, now Hologic, Inc., WI, USA) is a non-PCR based method and involves denaturing genomic DNA (25-50 min), preparing the Invader assay plates (adding mix, controls, standards, and DNA), incubating the plates on Thermo Cyclers or incubators (2-2½ hours), and reading the assay plate on the Tecan plate reader. The Invader assay, although novel in its kinetics, has many limitations. It is very time consuming and labor-intensive. Since it is a non-PCR based assay, it requires high-quality DNA and the result is highly variable if the concentration of DNA is sub-optimal (<11 ng/µl). If insufficient separation of RFU (relative fluorescence units) values is observed, an additional 30 minute incubation period is required and the plate will then be re-read.

TAQMAN (Roche Molecular Systems; see also e.g., Life Technologies Corp., Carlsbad Calif.) is a method of detecting and quantifying the presence of a DNA sequence. Briefly, a FRET oligonucleotide probe is designed with one oligo within the transgene and one in the flanking genomic sequence for event-specific detection. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection. Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal indicates the presence of the flanking genomic/transgene insert sequence due to successful amplification and hybridization.

Another challenge, among many, is finding a suitable reference gene for a given test. For example, as stated in the abstract of Czechowski et al., "An exceptionally large set of data from Affymetrix ATH1 whole-genome GeneChip studies provided the means to identify a new generation of reference genes with very stable expression levels in the model plant species *Arabidopsis* (*Arabidopsis thaliana*). Hundreds of *Arabidopsis* genes were found that outperform traditional reference genes in terms of expression stability throughout development and under a range of environmental conditions." (Czechowski et al. (2005) Genome-wide identification and testing of superior reference genes for transcript normalization in *Arabidopsis*. *Plant Physiol.* 139, 5-17.)

Brodmann et al. (2002) relates to real-time quantitative PCR detection of transgenic maize content in food for four different maize varieties approved in the European Union. Brodmann, P. D., P. D., Ilg E. C., Berthoud H., and Herrmann, A. Real-Time Quantitative Polymerase Chain Reaction Methods for Four Genetically Modified Maize Varieties and Maize DNA Content in Food. *J. of AOAC international* 2002 85 (3).

Baeumler et al. relates to a real-time quantitative PCR detection method specific to WIDESTRIKE transgenic cotton. *J. Agric. Food Chem.* (2006) 54(18), 6527-6534.

Hernandez et al. (2004) mentions four possible genes for use with real-time PCR. Hernandez, M., Duplan, M.-N., Berthier, G., Vaitilingom, M., Hauser, W., Freyer, R., Pla, M., and Bertheau, Y. Development and comparison of four real-time polymerase chain reaction systems for specific detection and quantification of *Zea mays* L. *J. Agric. Food Chem.* 2004, 52, 4632-4637.

Costa et al. (2007) looked at these four genes (also in the real-time PCR context) and concluded that the alcohol dehydrogenase and zein genes were the best reference genes for detecting a sample "event" (a lectin gene) for transgenic feed intermix issues. Costa, L. D., and Martinelli L. Development of a Real-Time PCR Method Based on Duplo Target Plasmids for Determining an Unexpected Genetically Modified Soybean Intermix with Feed Components. *J. Agric. Food Chem.* 2007, 55, 1264-1273.

Huang et al. (2004) used plasmid pMulM2 as reference molecules for detection of MON810 and NK603 transgenes in maize. Huang and Pan, "Detection of Genetically Modified Cotton MON810 and NK603 by Multiplex and Real-Time Polymerase Chain Reaction Methods," *J. Agric. Food Chem.*, 2004, 52 (11), pp 3264-3268.

Gasparic et al. (2008) suggest LNA technology, from a comparison to cycling probe technology, TaqMan, and various real-time PCR chemistries, for quantitatively analyzing cotton events (such as MON810). Gašparič, Cankar, Žel, and Gruden, "Comparison of different real-time PCR chemistries and their suitability for detection and quantification of genetically modified organisms," BMC Biotechnol. 2008; 8: 26.

US 20070148646 relates to a primer extension method for quantification that requires controlled dispensation of individual nucleotides that can be detected and quantified by the amount of nucleotides incorporated. This is different from the TaqMan PCR method using an internal reference gene.

To distinguish between homozygous and hemizygous genotypes of corn event TC1507, an Invader assay has been successfully used for this event. Gupta, M., Nirunsuksiri, W., Schulenberg, G., Hartl, T., Novak, S., Bryan, J., Vanopdorp, N., Bing, J. and Thompson, S. A non-PCR-based Invader Assay Quantitatively Detects Single-Copy Genes in Complex Plant Genomes. Mol. Breeding 2008, 21, 173-181.

Huabang (2009) relates to PCR-based zygosity testing of transgenic maize. However, no reference gene appears to be used. Huabang, "An Accurate and Rapid PCR-Based Zygosity Testing Method for Genetically Modified Maize," Molecular Plant Breeding, 2009, Vol. 7, No. 3, 619-623.

BRIEF SUMMARY OF THE INVENTION

The present invention relates in part to a molecular assay for determining zygosity of event 3006-210-23 in cotton. More specifically, the present invention relates in part to an endpoint TaqMan PCR assay for a WIDESTRIKE cry1Ac event 3006-210-23 in cotton utilizing endogenous reference genomic DNA in cotton. Some embodiments are directed to assays that are capable of high throughput zygosity analysis. The subject assays offer a reliable, consistent, and cost effective option. Some preferred assays are fluorescence-based and consist of a PCR set-up with the plate being subsequently read on a plate reader. This eliminates the denaturation step and the need for long incubation periods. Thus, the subject assays improve time, labor and cost efficiency.

The subject assays can be used for event-specific (3006-210-23) detection of the cry1Ac transgene in cotton plants by end-point TaqMan PCR. This TaqMan PCR based zygosity assay is a biplex assay. Some of the subject assays use oligonucleotides specific to the 3006-210-23 event and its flanking genomic sequences; some other assays utilize oligonucleotides corresponding to cotton genomic DNA used as a reference sequence in a single reaction. Zygosity is determined by the relative intensity of fluorescence specific for Event 3006-210-23 to the reference sequence.

In one embodiment, an exemplified 3006-210-23 event-specific assay amplifies a 281-bp fragment, unique to the event resulting from the insertion of the 3006-210-23 construct cassette into the cotton genomic DNA. A target-specific oligonucleotide probe binds to the target between two PCR primers (as exemplified, WT_R9, complementary to the 3' flanking genomic sequence, and WT_F9, complementary to the 3' end of the cry1Ac-containing insert) and is labeled with fluorescent dye (reporter dye) at its 5' end and a quencher (such as MGBNFQ (minor grove binding non-fluorescent quencher)) at its 3' end. PCR products are measured after optimal number of cycles, when the reaction is in the early exponential phase.

Due to the polyploidy nature of the cotton and molecular structure of the Event 3006-210-23, oligos specific to the flanking cotton genomic sequences of this event amplify in all individual plants of segregating populations, and thus can be used to separate wild-type from homozygotes in a plus/minus matter. Thus, genome-sequence-specific oligos were used as a reference for relative quantitation of genomic DNA.

This is a fluorescence-based end-point assay that allows the results to be directly read in a plate reader for identification of Event 3006-210-23 in cotton. The amplicons generated are not intended to be resolved on agarose gels.

In some preferred embodiments, the subject protocols are preferably used for breeding applications, i.e., testing related to introgression of a WIDESTRIKE event into other cotton lines.

SEQUENCE RULES COMPLIANCE

Figure 1:
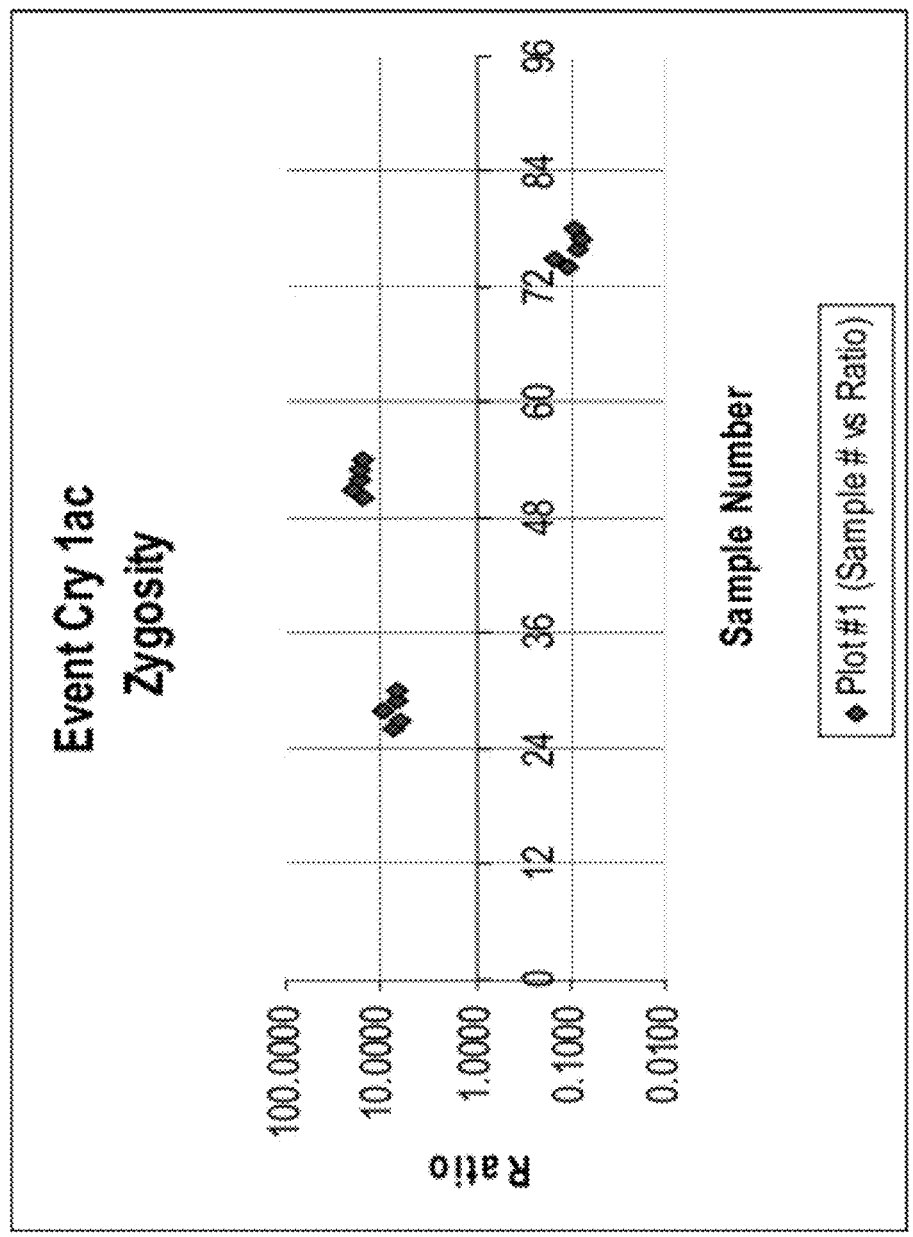
FIG. 1 shows results of a plate reader for RFU measurement and control validation.

SEQ ID NO:1 is the DNA sequence for the cry1Ac event 3006-210-23 insert and its border/flanking sequences.

SEQ ID NOs:2-7 are exemplified primers and probes for use according to the subject invention.

SEQ ID NO:8 is the transgene amplicon.

SEQ ID NO:9 is the wild-type amplicon.

DETAILED DESCRIPTION OF THE INVENTION

The subject invention relates in part to a fluorescence-based endpoint TaqMan PCR assay utilizing endogenous cotton genomic DNA as a reference control for high-throughput zygosity analysis of 3006-210-23, a cotton Cry1Ac event.

The subject invention also relates in part to the development of a biplex endpoint TaqMan PCR for 3006-210-23 event specific zygosity analysis. Further, the subject invention relates in part to the development of 3006-210-23 breeding test kits.

Endpoint TaqMan assays are based on a plus/minus strategy, by which a "plus" signifies the sample is positive for the assayed gene and a "minus" signifies the sample is negative for the assayed gene. These assays typically utilize two sets of oligonucleotides for identifying the 3006-210-23 transgene sequence and the wild-type gene sequence respectively, as well as dual-labeled probes to measure the content of transgene and wild type sequence.

Although the Invader assay has been a robust technique for characterizing events, it is very sensitive to DNA quality. In addition, the assay requires a high quantity of DNA. Invader also requires an additional denaturing step which, if not handled properly, can render the Invader assay unsuccessful. Additionally, the longer assay time of the Invader assay is limited in its flexibility to efficiently handle large numbers of 3006-210-23 samples for analysis in a commercial setting. One main advantage of the subject invention is time savings and elimination of the denaturing step. The subject Endpoint TaqMan analysis for detecting 3006-210-23 events offers surprising advantages over Invader, particularly in analyzing large number of samples.

In one embodiment, the 3006-210-23 event-specific PCR reaction amplifies a 281-bp fragment (SEQ ID NO:8), unique to the event, resulting from the insertion of the 3006-210-23 construct cassette of SEQ ID NO:1 into the cotton genomic DNA. A 3006-210-23 target-specific oligonucleotide probe (SEQ ID NO:7) binds to the target between two PCR primers and is labeled with a fluorescent dye and quencher. Possible fluorescent labels include FAM as a reporter dye at the 3006-210-23 probe 5' end and a Black Hole Quencher 1 (BHQ1) as the quencher at the 3006-210-23 probe 3' end.

The primers and probes for the cry1Ac gene insert and the cotton endogenous DNA were tested for PCR efficiencies. Primer and probe combinations for the cotton endogenous DNA were exploited for multiplexing capabilities and end-point TaqMan zygosity assay.

In some embodiments, the subject zygosity assays utilize a biplex of oligonucleotides specific to the 3006-210-23 event and to the cotton endogenous DNA lacking the event (the flanking sequences lacking the cry1Ac insertion) in the same amplification assay. Zygosity is determined by the relative intensity of fluorescence specific for Event 3006-210-23 as compared to the reference DNA.

In some embodiments, the 3006-210-23 event-specific assay amplifies a 281-bp fragment (SEQ ID NO:8), unique to the event, resulting from the insertion of the 3006-210-23 construct cassette of SEQ ID NO:1 into the cotton genomic DNA. A target-specific oligonucleotide probe (SEQ ID NO:7) binds to the target between two event-specific 3006-210-23 PCR primers (SEQ ID NO: 2 and SEQ ID NO:3) and is labeled with two fluorescent dyes (such as FAM as a reporter dye at its 5' end and BHQ as a quencher dye at its 3' end). PCR products are measured after optimal number of cycles, typically when the reaction is in the early exponential phase.

In some embodiments, the fluorescence-based end-point TaqMan assay for 3006-210-23 zygosity analysis allows the results to be directly read in a plate reader for determining zygosity of the WIDESTRIKE Event 3006-210-23 in cotton (without use of a reference gene per se).

The subject invention includes breeding applications such as testing the introgression of WIDESTRIKE into other cotton lines.

Detection methods and kits of the subject invention can be used to identify events according to the subject invention. Methods and kits of the subject invention can be used for accelerated breeding strategies and to establish linkage data.

Detection techniques of the subject invention are especially useful in conjunction with plant breeding, to determine which progeny plants comprise a given event, after a parent plant comprising an event of interest is crossed with another plant line in an effort to impart one or more additional traits of interest in the progeny. These TaqMan PCR analysis methods benefit cotton breeding programs as well as quality control, especially for commercialized transgenic cotton seeds. TaqMan PCR detection kits for these transgenic cotton lines can also now be made and used. This can also benefit product registration and product stewardship.

Still further, the subject invention can be used to study and characterize transgene integration processes, genomic integration site characteristics, event sorting, stability of transgenes and their flanking sequences, and gene expression (especially related to gene silencing, transgene methylation patterns, position effects, and potential expression-related elements such as MARS [matrix attachment regions], and the like).

This invention further includes processes of making crosses using a 3006-210-23 plant as at least one parent. For example, the subject invention includes an $F_1$ hybrid plant having as one or both parents any of the plants exemplified herein. This invention includes a method for producing an $F_1$ hybrid seed by crossing an exemplified plant with a different (e.g. in-bred parent) plant, harvesting the resultant hybrid seed, and testing the seed/plant sample according to the subject invention. Characteristics of the resulting plants may be improved by careful consideration of the parent plants.

An insect-resistant cotton plant can be bred by first sexually crossing a first parental cotton plant consisting of a cotton plant grown from seed of any one of the lines referred to herein, and a second parental cotton plant, thereby producing a plurality of first progeny plants; and then selecting a first progeny plant that is resistant to insects (or that possesses at least one of the events of the subject invention); and selfing the first progeny plant, thereby producing a plurality of second progeny plants; and then selecting from the second progeny plants a plant that is resistant to insects (or that possesses at least one of the events of the subject invention). These steps can further include the back-crossing of the first progeny plant or the second progeny plant to the second parental cotton plant or a third parental cotton plant. A cotton crop comprising cotton seeds of the subject invention, or progeny thereof, can then be planted.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Other breeding methods commonly used for different traits and crops are known in the art. Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (back-crossed) to the recurrent parent. The resulting parent is expected to have the attributes of the recurrent parent (e.g., cultivar) and the desirable trait transferred from the donor parent.

DNA molecules of the present invention can be used with molecular markers in a marker assisted breeding (MAB) method. DNA molecules of the present invention can be used with methods (such as, AFLP markers, RFLP markers, RAPD markers, SNPs, and SSRs) that identify genetically linked agronomically useful traits, as is known in the art. The insect-resistance trait can be tracked in the progeny of a cross with a cotton plant of the subject invention (or progeny thereof and any other cotton cultivar or variety) using the MAB methods. The DNA molecules are markers for this trait, and MAB methods that are well-known in the art can be used to track the insect-resistance trait(s) in cotton plants where at least one cotton line of the subject invention, or progeny thereof, was a parent or ancestor. The methods of the present invention can be used to identify any cotton variety having the insect-resistance event from cotton line 3006-210-23.

Methods of the subject invention include a method of producing an insect-resistant cotton plant wherein said method comprises breeding with a plant of the subject invention. More specifically, said methods can comprise crossing two plants of the subject invention, or one plant of the subject invention and any other plant, and tracking the subject event according to the subject invention. Preferred methods further comprise selecting progeny of said cross by analyzing said progeny for an event detectable according to the subject invention.

A preferred plant, or a seed, propagated and developed according to the subject invention comprises in its genome at least one of the insert sequences (residues 528-8900 of SEQ ID NO:1) together with at least 20-500 or more contiguous flanking nucleotides on both sides of the insert (residues 1-527 and 8901-9382 of SEQ ID NO:1). Unless indicated otherwise, "event 3006-210-23" or like reference refers to DNA of SEQ ID NO:1 that includes the heterologous DNA inserted in the genomic location identified by all or part of both of the flanking genomic sequences immediately adjacent to the inserted DNA that would be expected to be transferred to progeny that receives the inserted DNA as a result of a sexual cross of a parental line that includes the event.

Definitions and examples are provided herein to help describe the present invention and to guide those of ordinary skill in the art to practice the invention. Unless otherwise noted, terms are to be understood according to conventional usage by those of ordinary skill in the relevant art. The nomenclature for DNA bases as set forth at 37 CFR §1.822 is used.

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

A "junction sequence" spans the point at which DNA inserted into the genome is linked to DNA from the cotton native genome flanking the insertion point, the identification or detection of one or the other junction sequences in a plant's genetic material being sufficient to be diagnostic for the event. Included are the DNA sequences that span the insertions in herein-described cotton events and similar lengths of flanking DNA. Specific examples of such diagnostic sequences are provided herein; however, other sequences that overlap the junctions of the insertions, or the junctions of the insertions and the genomic sequence, are also diagnostic and could be used according to the subject invention.

Primers, amplicons, and probes can be designed for use according to the subject invention based in part on the flanking, junction, and/or insert sequences. Related primers and amplicons can be included as components of the invention. PCR analysis methods using amplicons that span across inserted DNA and its borders can be used to detect or identify commercialized transgenic cotton varieties or lines derived from the subject proprietary transgenic cotton lines.

The sequence of the cry1Ac insert (together with regulatory sequences), flanked by the flanking sequences is provided as SEQ ID NO:1. The coordinates of the insert and flanking sequences with respect to SEQ ID NO:1 are as follows: 5' flanking is residues 1-527, Event 3006-210-23 genetic insert is residues 528-8900, and 3' flanking sequence is residues 8901-9382.

This insertion event, including components thereof, is further illustrated in, for example, U.S. Pat. No. 7,179,965. Seed deposit information is also provided therein. Based on these insert and border sequences, event-specific primers were, and can be, generated. PCR analysis demonstrated that these cotton lines can be identified in different cotton genotypes by analysis of the PCR amplicons generated with these event-specific primer sets. Thus, these and other related procedures can be used to uniquely identify these cotton lines.

As used herein, a "line" is a group of plants that display little or no genetic variation between individuals for at least one trait. Such lines may be created by several generations of self-pollination and selection, or vegetative propagation from a single parent using tissue or cell culture techniques.

As used herein, the terms "cultivar" and "variety" are synonymous and refer to a line which is used for commercial production. "Stability" or "stable" means that with respect to the given component, the component is maintained from generation to generation and, preferably, at least three generations at substantially the same level, e.g., preferably ±15%, more preferably ±10%, most preferably ±5%. The stability may be affected by temperature, location, stress and the time of planting. Comparison of subsequent generations under field conditions should produce the component in a similar manner.

"Commercial Utility" is defined as having good plant vigor and high fertility, such that the crop can be produced by farmers using conventional farming equipment, and the oil with the described components can be extracted from the seed using conventional crushing and extraction equipment. To be commercially useful, the yield, as measured by seed weight, oil content, and total oil produced per acre, is within 15% of the average yield of an otherwise comparable commercial canola variety without the premium value traits grown in the same region.

"Agronomically elite" means that a line has desirable agronomic characteristics such as yield, maturity, disease resistance, and the like, in addition to the insect resistance due to the subject event(s).

As one skilled in the art will recognize in light of this disclosure, preferred embodiments of detection kits, for example, can include probes and/or primers directed to and/or comprising "junction sequences" or "transition sequences" (where the cotton genomic flanking sequence meets the insert sequence). For example, this includes a polynucleotide probe, primer, or amplicon comprising a sequence including residues, as indicated in Table 1. Some preferred primers can include at least ~15 residues of the adjacent flanking sequence and at least ~15 residues of the adjacent insert sequence. Residues within 200 bases or so of the junction sequences can be targeted. With this arrangement, another primer in either the flanking or insert region can be used to generate a detectable amplicon that indicates the presence of an event of the subject invention. In some preferred embodiments, one primer binds in the flanking region and one binds in the insert, and these primers can be used to generate an amplicon that spans (and includes) a junction sequence.

One skilled in the art will also recognize that primers and probes can be designed to hybridize, under a range of standard hybridization and/or PCR conditions, to a segment of SEQ ID NO:1, and complements thereof, wherein the primer or probe is not perfectly complementary to the exemplified sequence. That is, some degree of mismatch can be tolerated. For an approximately 20 nucleotide primer, for example, typically one or two or so nucleotides do not need to bind with the opposite strand if the mismatched base is internal or on the end of the primer that is opposite the amplicon. Various appropriate hybridization conditions are provided below. Synthetic nucleotide analogs, such as inosine, can also be used in probes. Peptide nucleic acid (PNA) probes, as well as DNA and RNA probes, can also be used. What is important is that such probes and primers are diagnostic for (able to uniquely identify and distinguish) the presence of an event of the subject invention.

Components of the transgene "insert" or construct are disclosed in, for example, U.S. Pat. No. 7,179,965. Polynucleotide sequences or fragments of these components can be used as DNA primers or probes in the methods of the present invention.

In some embodiments of the invention, compositions and methods are provided for detecting the number of copies of the transgene/genomic insertion region, in plants and seeds and the like, from a cotton plant designated WIDESTRIKE comprising Cry1Ac event 3006-210-23. DNA sequences are provided that comprise at least one transgene/genomic insertion region junction sequence provided herein in SEQ ID NO:1, segments thereof, and complements of the exemplified sequences and any segments thereof. The insertion region junction sequence spans the junction between heterologous DNA inserted into the genome and the DNA from the cotton cell flanking the insertion site. Such sequences are diagnostic for the subject event.

Based on these insert and border sequences, event-specific primers were generated. TaqMan PCR analysis of the subject invention demonstrated that cotton event 3006-210-23 can be identified in different cotton lines and genotypes by analysis of the PCR amplicons generated with these event-specific primer sets. These and other related procedures can be used to uniquely identify these cotton lines.

In some embodiments, DNA sequences that comprise (or are complementary, at least in part) to a contiguous portion/segment of the transgene/genomic insertion regions are an aspect of this invention. Included are DNA sequences that comprise a sufficient length of polynucleotides of transgene insert sequence and a sufficient length of polynucleotides of cotton genomic sequence from one or more of the subject cotton plants.

Related embodiments pertain to DNA sequences that comprise at least 2, 3, 4, 5, 6, 7, 8, 9, 10, 11, 12, 13, 14, 15, 16, 17, 18, 19, 20, 21, 22, 23, 24, 25, or more contiguous nucleotides of a transgene portion of a DNA sequence of SEQ ID NO:11, or complements thereof, and a similar length of flanking cotton DNA sequence, or complements thereof. Such sequences are useful as, for example, DNA primers in DNA amplification methods. Components of the invention also includes the amplicons produced by such DNA primers and homologous primers.

This invention also includes methods of detecting the presence of DNA, in a sample, from at least one of the cotton plants referred to herein. Such methods can comprise: (a) contacting the sample comprising DNA with a primer set that, when used in a nucleic acid amplification reaction, of the subject invention, with DNA from at least one of these cotton events; (b) performing a TAQMAN PCR amplification reaction using reference DNA identified herein; and (c) analyzing the results.

In still further embodiments, the subject invention includes methods of producing a cotton plant comprising a cry1Ac event of the subject invention, wherein said method comprises the steps of: (a) sexually crossing a first parental cotton line (comprising an expression cassettes of the present invention, which confers said insect resistance trait to plants of said line) and a second parental cotton line (that lacks this insect tolerance trait) thereby producing a plurality of progeny plants; and (b) selecting a progeny plant based on results of at least one assay technique of the subject invention. Such methods may optionally comprise the further step of back-crossing the progeny plant to the second parental cotton line to producing a true-breeding cotton plant that comprises said insect tolerance trait. According to another aspect of the invention, related methods of determining the zygosity of progeny of a cross are provided.

DNA detection kits can be developed using the compositions disclosed herein and methods well known in the art of DNA detection. The kits are useful for identification of the subject cotton event DNA in a sample and can be applied to methods for breeding cotton plants containing this DNA. The kits contain DNA sequences homologous or complementary to the amplicons, for example, disclosed herein, or to DNA sequences homologous or complementary to DNA contained in the transgene genetic elements of the subject events. These DNA sequences can be used in DNA amplification reactions or as probes in a DNA hybridization method. The kits may also contain the reagents and materials necessary for the performance of the detection method.

A "probe" is an isolated nucleic acid molecule to which is attached a conventional detectable label or reporter molecule (such as a radioactive isotope, ligand, chemiluminescent agent, or enzyme). Such a probe is complementary to a strand of a target nucleic acid, in the case of the present invention, to a strand of genomic DNA from one of said cotton events, whether from a cotton plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated nucleic acids that are annealed to a complementary target DNA strand by nucleic acid hybridization to form a hybrid between the primer and the target DNA strand, and can be used in conjunction with a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers (and amplicons) are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 polynucleotides or more in length. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods.

Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989. Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52 and 9.56-9.58. Accordingly, the nucleotide sequences of the invention may be used for their ability to selectively form duplex molecules with complementary stretches of DNA fragments.

Depending on the application envisioned, one can use varying conditions of hybridization to achieve varying degrees of selectivity of probe towards target sequence. For applications requiring high selectivity, one will typically employ relatively stringent conditions to form the hybrids, e.g., one will select relatively low salt and/or high temperature conditions, such as provided by about 0.02 M to about 0.15 M NaCl at temperatures of about 50° C. to about 70° C. Stringent conditions, for example, could involve washing the hybridization filter at least twice with high-stringency wash buffer (0.2×SSC, 0.1% SDS, 65° C.). Appropriate stringency conditions which promote DNA hybridization, for example, 6.0× sodium chloride/sodium citrate (SSC) at about 45° C., followed by a wash of 2.0×SSC at 50° C. are known to those skilled in the art, 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well-known to those of skill in the art, and the teachings of U.S. Pat. Nos. 4,965,188 and 5,176,995 are exemplary of the methods of hybridization analyses.

In a particularly preferred embodiment, a nucleic acid of the present invention will specifically hybridize to one or more of the primers (or amplicons or other sequences) exemplified or suggested herein, including complements and fragments thereof, under high stringency conditions. In one aspect of the present invention, a nucleic acid molecule of the present invention has the nucleic acid sequence set forth in SEQ ID NOs:2-7, or complements and/or fragments thereof.

In another aspect of the present invention, a marker nucleic acid molecule of the present invention shares between 80% and 100% or 90% and 100% sequence identity with such nucleic acid sequences. In a further aspect of the present invention, a nucleic acid molecule of the present invention shares between 95% and 100% sequence identity with such sequence. Such sequences may be used in plant breeding methods, for example, to identify the progeny of genetic crosses. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the cotton plant resulting from a sexual cross contains transgenic event genomic DNA from the cotton plant of the present invention, DNA extracted from a cotton plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, and/or the combined length of the primer pairs plus about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500, 750, 1000, 1250, 1500, 1750, 2000, or more nucleotide base pairs (plus or minus any of the increments listed above). Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA sequence. This distance can range from one nucleotide base pair up to about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202. PCR amplification methods have been developed to amplify up to 22 kb of genomic DNA. These methods as well as other methods known in the art of DNA amplification may be used in the practice of the present invention. The sequence of the heterologous transgene DNA insert or flanking genomic sequence from a subject cotton event can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. Agarose gel electrophoresis and staining with ethidium bromide is a common well known method of detecting DNA amplicons. Another such method is Genetic Bit Analysis where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

All patents, patent applications, provisional applications, and publications referred to or cited herein are incorporated by reference in their entirety to the extent they are not inconsistent with the explicit teachings of this specification.

EXAMPLES

Example 1

Extraction of Genomic DNA

DNA was extracted from cotton leaf tissue obtained from a single plant using QIAGEN's DNeasy 96 Plant Kit (Qiagen, Valencia, Calif.). The QIAGEN protocol was implemented according to manufacturer's recommendation with a few modifications for the cotton DNA extraction as follows: A final concentration of 10 mM sodium metabisulfite was added during cell lysis and a final concentration of 10 mM DTT was added to the final DNA (Horne et al., 2004). DNA was quantified using PicoGreen® dye from Molecular Probes, Inc. (Eugene, Oreg.). Each well of a microtiter plate contained 100 µl of 200-fold picogreen combined with 5 µl of DNA sample or Lambda DNA standards (0, 2.5, 5, and 10 ng/µl). Plates were shaken briefly using standard plate shaker and read using SpectraMax®fluorometer from Molecular Devices (Sunnyvale, Calif.). The DNA sample concentrations were diluted to 12 ng/µl with sterile water.

Example 2

Primer Design and Selection

Primers and probes (a fluorophore at 5' end and a Black Hole Quencher™ at 3'end) were designed for both the wild type and transgene using Primer Express® software, version 3.0 (Applied Biosystems, Inc., Foster City, Calif.) and Vector NTI® software, (Invitrogen Corp., Carlsbad, Calif.). Forward and reverse primers were paired, PCR was performed and the results were analyzed by gel electrophoresis (2% agarose e-gel). The most promising candidates were then paired with probes and run on real time PCR. Based on the results from the real time PCR, a transgene primer pair and a wild type primer pair with respective probes were chosen.

Example 3

Standard PCR Conditions

Probes were labeled with different fluorescent dyes (FAM-490 for transgene and Texas Red for wild type). PCR reactions were performed in a final volume of 25 µl containing: 0.2 µM of the common event primer and the transgene forward primer, 0.4 µM of the wild-type forward primer, 0.08 µM of each probe, 0.3 mM of dNTP, 4 mM $MgCl_2$, 2.5 µl of 10% PVP-40, 1 unit of HotStarTaq DNA polymerase (Qiagen, Valencia, Calif.), and 36 ng of template DNA. PVP-40 was added to the reaction to improve PCR fidelity (Horne et al, 2004). PCR reactions were run on GeneAmp® PCR System 9700 Thermocyclers (Applied Biosystems, Inc., Foster City, Calif.) using the following cycling conditions: Individual wild type and transgene PCR reactions denatured at 95° C. for 15 min; 40 cycles of 95° C. for 30 sec, 60° C. for 30 sec. 72° C. for 30 sec, followed by a final extension at 72.0° C. for 5 min. Combined PCR reaction—95° C. for 15 min; 35 cycles of 95° C. for 15 sec, 60° C. for 1 min, followed by a final extension at 72° C. for 5 min.

Example 4

Preparation of PCR Protocol

An existing Cotton 3006 Cry1Ac protocol and a published protocol entitled "Event Specific Method for the Quantification of Cotton 3006-210-23 Using Real-Time PCR" were reviewed. [Horne, E. C., S. P. Kumpatla, K. A. Patterson, M. Gupta and S. A. Thompson. 2004. Improved high-throughput sunflower and cotton genomic DNA extraction and PCR fidelity. Plant Molecular Biology Reporter 22:93a-83i.] [Protocol cotton 3006-210-23 —Community Reference Laboratory for GM Food and Feed. Method validated by Joint Research Centre—European Commission. Biotechnology & GMOs Unit. CRLVL14/05VP. Apr. 21, 2006.] See also U.S. Pat. No. 7,179,965. The concentrations of reagents used in the two protocols were averaged and an initial PCR recipe was generated (Table 1).

TABLE 1

The initial TaqMan ® protocol

| Component | Final Concentration | µl/Reaction |
|---|---|---|
| H2O | | 11.55 |
| 10 X Buffer (15 mM MgCl2) | 1 X | 2.5 |
| 10% PVP | 1 X | 2.5 |
| dNTP (10 mM) | 0.3 mM | 0.75 |
| MgCl2 (25 mM)* | 4 mM | 4.0 |
| Common Event Primer (20 uM) 3006_WT_R9 SEQ ID NO: 2 | 0.2 uM | 0.25 |
| Transgene Forward Primer (20 uM) 3006_WT_F9 SEQ ID NO: 3 | 0.2 uM | 0.25 |
| Transgene Probe (10 uM) 3006_IAC_Probe_8796 SEQ ID NO: 5 | 0.08 uM | 0.20 |
| Wild Type Forward Primer (20 uM) 3006_WT_F6 SEQ ID NO: 4 | 0.2 uM | 0.25 |
| Wild Type Probe (10 uM) 3006_WT_P6 SEQ ID NO: 7 | 0.08 uM | 0.20 |
| Qiagen Taq Polymerase (5 U/µl) | 1 U/rxn | 0.20 |
| *Total $MgCl_2$ = 3.5 mM | Add 3 µl of DNA | 25 µl total volume/reaction |

This recipe, along with previously designed primers and controls, was used to generate a baseline PCR reaction. A gradient PCR was run (temperature range of 50° C.-66° C.) and E-gel analysis was used to determine the optimal temperature. Initial gels showed low specificity, so $MgCl_2$ and dNTP concentrations were adjusted. Temperatures 60° C. and 55° C. were chosen as the most efficient annealing temperatures. The transgene PCR reaction and the wild type PCR reaction were run separately at this point.

Example 5

Selection of Probes and Primer Pairs

Primer pairs #1 through #7 (forward and reverse) were previously designed and an additional 15 new primers were designed.

Forward and reverse primers (20 uM) were paired (see Table 2), combined with PCR recipe and run on gradient PCRs with annealing temperatures ranging from 45° C. to 66° C. The best results were found using primer pairs #13, #14, #20, #21, and #22 at 55° C. and 60° C. annealing temperatures.

TABLE 2

| Probe | Forward Primer | Reverse Primer |
| --- | --- | --- |
| 3006_IAC_Probe_8796 SEQ ID NO: 5 | 3006_WT_F9 SEQ ID NO: 3 | 3006_WT_R9 SEQ ID NO: 2 |
| Probe 3006_WT_P6 SEQ ID NO: 7 | 3006_WT_F6 SEQ ID NO: 4 | 3006_WT_R9 SEQ ID NO: 2 |
| Probe 3006_WT_P4 SEQ ID NO: 6 | | |

3006_WT_P4 and 3006_WT_P6 were labeled with Texas Red dye for use as probes in the transgene PCR reaction and 3006_IAC_Probe_8796, and 3006_TG_P2 were labeled with FAM-490 dye for use as probes in the wild type PCR reaction. Primer pairs #13 and #14 were combined with 3006_IAC_Probe_8796 and 3006_TG_P2 probes. Primer pairs #20, #21, and #22 were combined with 3006_WT_P4 and 3006_WT_P6 probes. Sequences for these primers and probes are given in Table 3.

TABLE 3

Primer/Probe Sequences utilized to validate and optimize the Cry1Ac TaqMan ® assay.

| Name | Oligonucleotide DNA Sequence (5' to 3') | SEQ ID NO: |
| --- | --- | --- |
| Common Event Primer 3006_WT_R9 | 5'-GAT AAA TTT GCT AAA CAT GAC TAA ACA CTA-3' | 2 |
| Transgene Forward Primer 3006_WT_F9 | 5'-ATG GAT CAT TAA TTT CCA CCT TCA C-3' | 3 |
| Wild Type Forward Primer 3006_WT_F6 | 5-TTA AGA CGT AAA GTA TTA CAT CGA AGG G-3' | 4 |
| Transgene Probe 3006_IAC_Probe_8796 | 5'-TAT TGT ACG GCT AAG AGC GAA TTT GGC C-3' | 5 |
| Wild Type Probe 3006_WT_P4 | 5'-TTC AAT TTC ATG CTC ATC CAC TCG TTT CA-3' | 6 |
| Wild Type Probe 3006_WT_P6 | 5'-TCA ATT ATT CAG AAC GTT TCC-3' | 7 |

Figure 3:
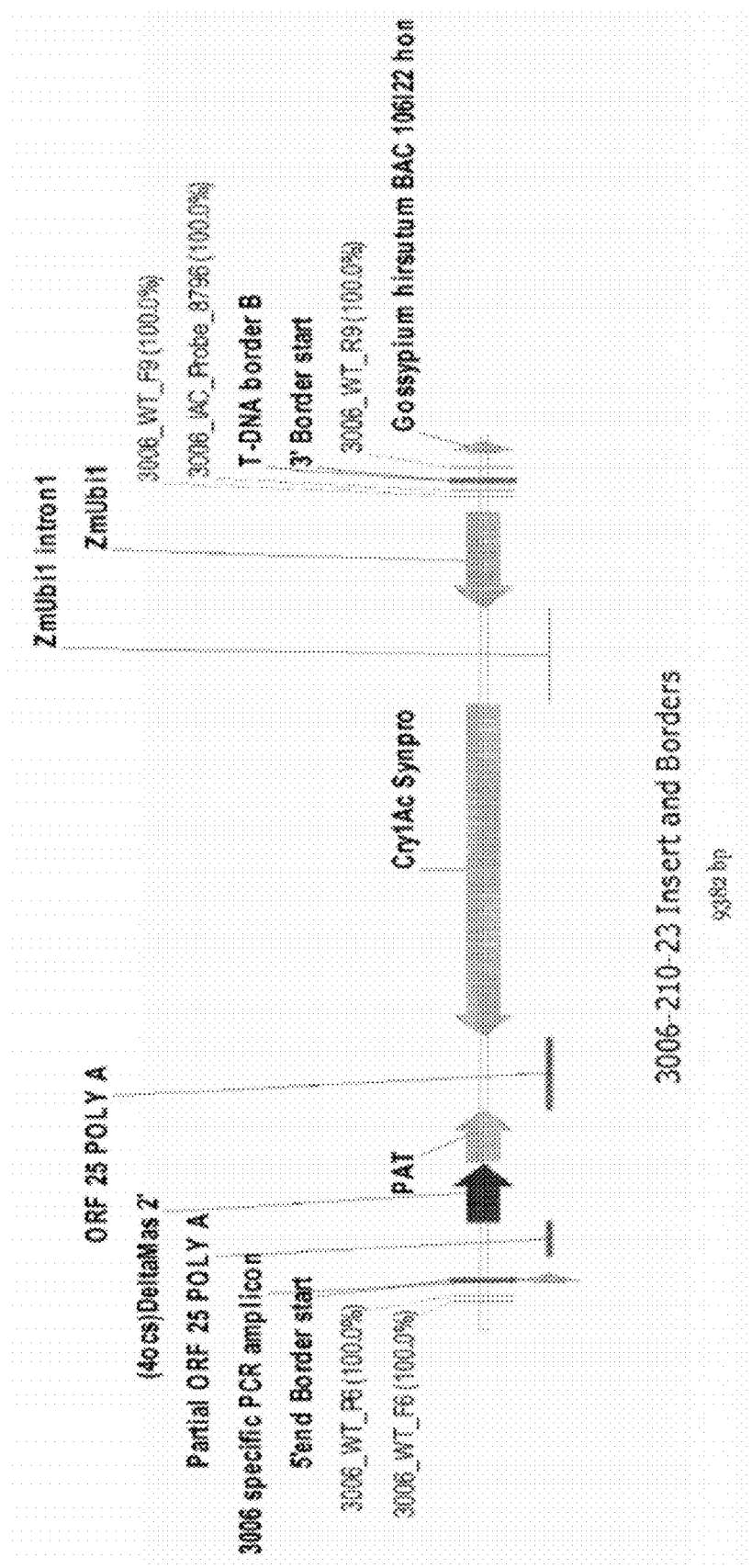
FIG. 3 illustrates the locational relationship of the wild-type primers. The 100% in the parenthesis after each SEQ ID NO indicates 100% match to the SEQ ID NO it follows.
Figure 4:
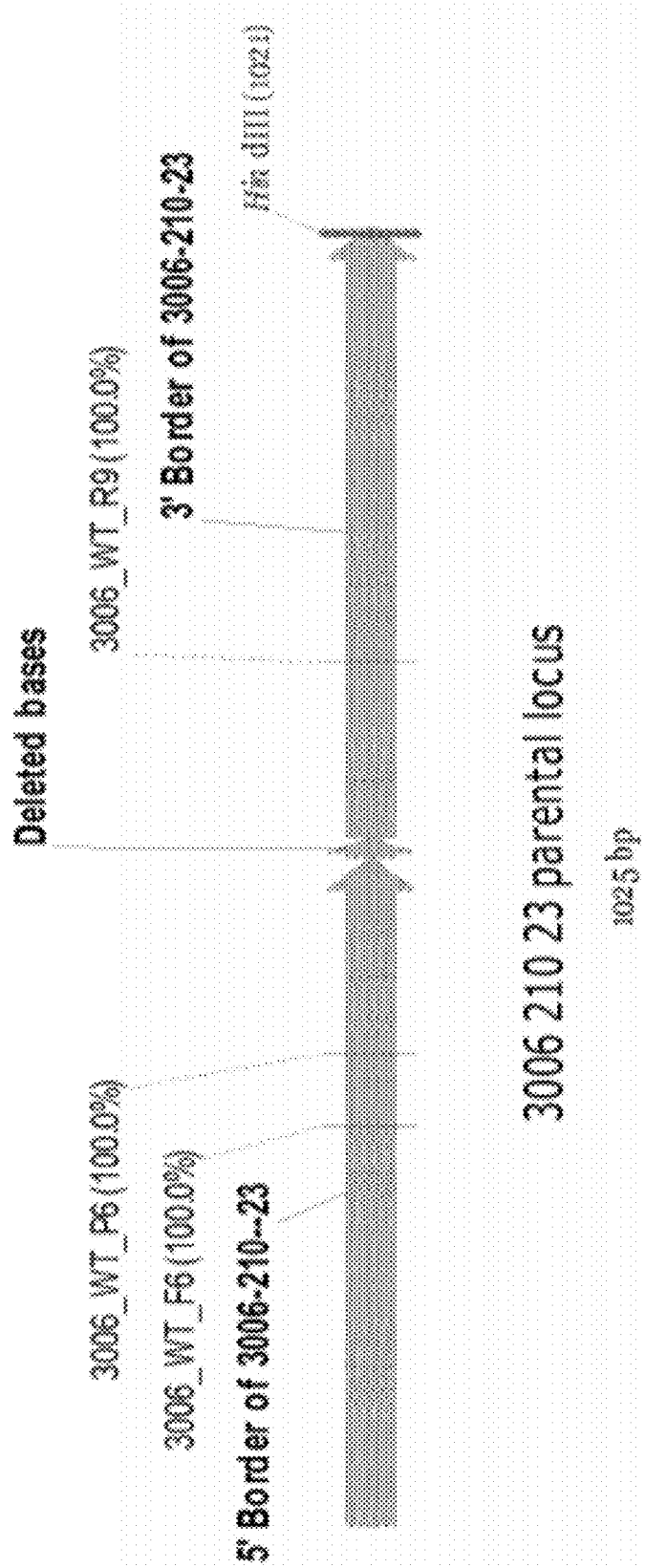
FIG. 4 illustrates the locational relationship of the transgene primers. The 100% in the parenthesis after each SEQ ID NO indicates 100% match to the SEQ ID NO it follows.

The transgene amplicon (SEQ ID NO:8) is 325 basepairs. See FIG. 3. The wild-type amplicon is provided as SEQ ID NO:9. See FIG. 4.

Table 4 shows the plate layout for the real-time PCR reaction.

TABLE 4

Real-Time PCR Plate Layout.

| | 1 | 2 | 3 | 4 | 5 | 6 | 7 | 8 | 9 | 10 | 11 | 12 |
| --- | --- | --- | --- | --- | --- | --- | --- | --- | --- | --- | --- | --- |
| A | 13 IAC HMZ | 13 IAC Hemi | 13 IAC Null | 13 IAC NT | 13 P2 HMZ | 13 P2 Hemi | 13 P2 Null | 13 P2 NT | 14 IAC HMZ | 14 IAC Hemi | 14 IAC Null | 14 IAC NT |
| B | 13 IAC HMZ | 13 IAC Hemi | 13 IAC Null | 13 IAC NT | 13 P2 HMZ | 13 P2 Hemi | 13 P2 Null | 13 P2 NT | 14 IAC HMZ | 14 IAC Hemi | 14 IAC Null | 14 IAC NT |
| C | | | | | Blank | | | | | | | |
| D | 14 P2 HMZ | 14 P2 Hemi | 14 P2 Null | 14 P2 NT | 20 P4 HMZ | 20 P4 Hemi | 20 P4 Null | 20 P4 NT | 20 P6 HMZ | 20 P6 Hemi | 20 P6 Null | 20 P6 NT |
| E | 14 P2 HMZ | 14 P2 Hemi | 14 P2 Null | 14 P2 NT | 20 P4 HMZ | 20 P4 Hemi | 20 P4 Null | 20 P4 NT | 20 P6 HMZ | 20 P6 Hemi | 20 P6 Null | 20 P6 NT |
| F | | | | | Blank | | | | | | | |
| G | 21 P4 HMZ | 21 P4 Hemi | 21 P4 Null | 21 P4 NT | 21 P6 HMZ | 21 P6 Hemi | 21 P6 Null | 21 P6 NT | 22 P4 HMZ | 22 P4 Hemi | 22 P4 Null | 22 P4 NT |
| H | 21 P4 HMZ | 21 P4 Hemi | 21 P4 Null | 21 P4 NT | 21 P6 HMZ | 21 P6 Hemi | 21 P6 Null | 21 P6 NT | 22 P4 HMZ | 22 P4 Hemi | 22 P4 Null | 22 P4 NT |

Example 6

Real Time PCR Analysis

The protocol used for the real-time PCR is as follows:

| Cycle 1 (1X) | | |
|---|---|---|
| Step 1: | 95° C. | for 15:00 |
| Cycle 2 (40X) | | |
| Step 1: | 95° C. | for 00:30 |
| Step 2: | 60° C. | for 00:30 |
| (Data collection & real-time analysis enabled at this step) | | |
| Step 3: | 72° C. | for 00:30 |
| Cycle 3 (1X) | | |
| Step 1: | 72° C. | for 05:00 |
| Step 2: | 4° C. | HOLD |

Data parameters for real-time PCR are: "Calculated threshold has been replaced by the user selected threshold 57.6. Per-well baseline cycles have been determined automatically. Data analysis window is set at 95.00% of a cycle, centered at end of the cycle. Weighted Mean digital filtering has been applied. Global filtering is off." The results of the real-time PCR showed 60° C. (rather than 55° C.) to be a better temperature (more specific) for the reaction. Primer set #20 with probe 3006_WT_P4 showed optimal amplification between 27.9 and 30.3 cycles. Primer set #14 with probe 3006_IAC_Probe_8796 showed optimal amplification between 27.6 and 29.2 cycles.

A real-time PCR reaction was set-up with a 60° C. annealing temperature and both the transgene and the wild type PCR reactions were combined. The results showed optimal amplification between 25.6 and 28.2 cycles. Based on these results and to reduce the overall PCR reaction time, the number of PCR cycles was reduced to 35 and the PCR reaction was reduced to a 2-step reaction with the 95° C. denaturation time reduced to 15 seconds and the 60° C. annealing/extension steps of the protocol combined for a total time of 60 seconds.

Example 7

Control Validation

Event positive and negative control seeds previously tested using the INVADER zygosity assay system (Third Wave Technologies, Inc.) were used. DNA prepared from controls were labeled as either hemizygous, homozygous, or null. These DNA samples were normalized to 12 ng/µl and tested with the TaqMan® PCR-based assay.

A PCR master mix was prepared with 22 µl of mix and 3 µl of normalized DNA added to each well. Five (5) replicates of each control (hemi, homo and null) were tested and read on the Tecan plate reader for RFU measurement. A plus/minus analysis of the results was performed and all controls tested as expected. Results can be found in FIG. 1.

Example 8

PCR Validation

Figure 2:
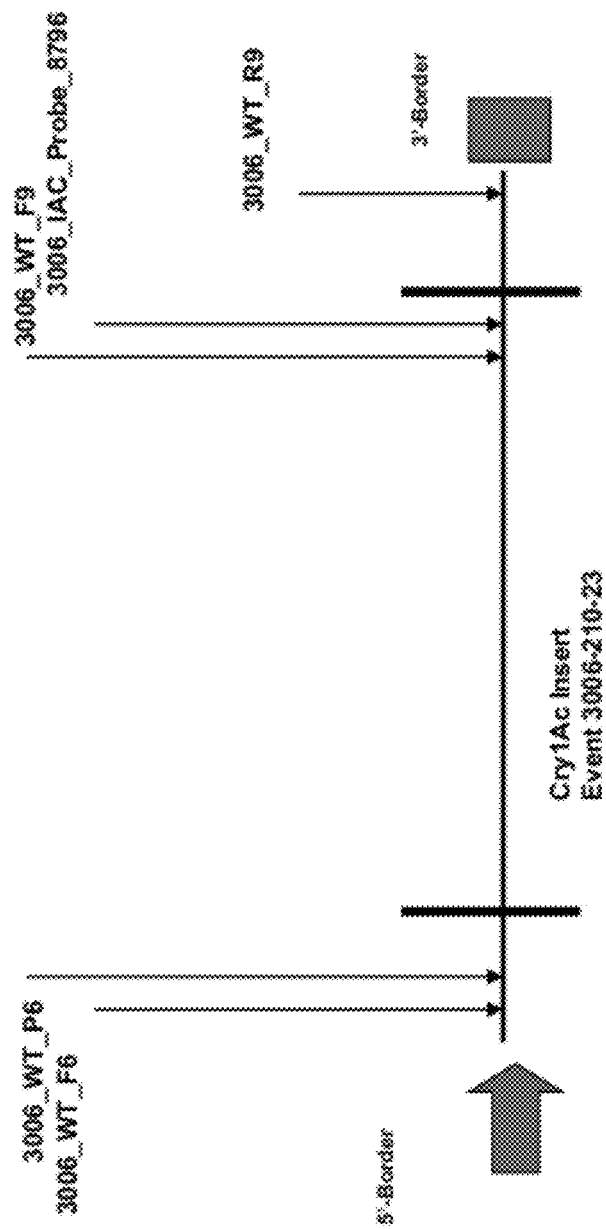
FIG. 2 shows the location of primers and probes for zygosity determination with respect to the cry1Ac event.

The PCR recipe was adjusted to reflect the common event primer (3006_WT_R9) being used for both reactions (see FIG. 2) and a sample plate was run using normalized cotton DNA (12 ng/µl). The PCR product was then read on the Tecan plate reader and analyzed using a plus/minus analysis method. Zygosity calls were made and compared to calls generated from the existing Invader assay under the assumption that Invader calls were correct. The TaqMan assay had 15 out of 90 calls made differently (17%) when compared to the Invader assay.

To improve the results, the WT forward primer and the WT probe were each doubled in separate PCR reactions and both were doubled in a third reaction. This was done to obtain higher RFU values in our unknown DNA samples and to create greater separation of the RFU values for the negative and positive controls. Results from this modification showed the 2× wild type forward primer to be most promising. During this step in the validation process, problems repeatedly occurred with the 3006_WT_P4 probe (high background) and the Tecan plate reader so a new probe was ordered that was labeled with a different dye. The background issues continued and eventually the back-up probe (3006_WT_P6 labeled with Texas Red dye) was used to replace the original probe for the wild type reaction.

TABLE 5

The final and optimized TaqMan ® based PCR protocol for Cry1Ac detection.

| Component | Final Concentration | µl/Reaction |
|---|---|---|
| H2O | | 12.15 |
| 10 X Buffer (15 mM MgCl2) | 1 X | 2.5 |
| 10% PVP | 1 X | 2.5 |
| dNTP (10 mM) | 0.5 mM | 1.25 |
| MgCl2 (25 mM)* | 2 mM | 2.0 |
| Common Event Primer (20 uM) 3006_WT_R9 SEQ ID NO: 2 | 0.2 uM | 0.25 |
| Transgene Forward Primer (20 uM) 3006_WT_F9 SEQ ID NO: 3 | 0.2 uM | 0.25 |
| Transgene Probe (10 uM) 3006_IAC_Probe_8796 SEQ ID NO: 5 | 0.08 uM | 0.20 |
| Wild Type Forward Primer (20 uM) 3006_WT_F6 SEQ ID NO: 4 | 0.4 uM | 0.50 |
| Wild Type Probe (10 uM) 3006_WT_P6 SEQ ID NO: 7 | 0.08 uM | 0.20 |
| Qiagen Taq Polymerase (5 U/µl) | 1 U/rxn | 0.20 |
| *Total MgCl$_2$ = 3.5 mM | Add 3 µl of DNA | 25 µl total volume/reaction |

Validation of the PCR recipe was performed using 4 DNA plates (Cotton Cotyledon Boxes 3, 4, 5 & 6). The results were compared to Invader results and it was found that the calls (hemi, homo or null) from both assays matched an average of 95.85%. Cotton Cotyledon Box 3 had 77 samples analyzed and 6 calls differed (92.2% same); Cotton Cotyledon Box 4 had 74 samples analyzed and 3 calls differed (95.9% same); Cotton Cotyledon Box 5 had 72 samples analyzed and 2 calls differed (97.2% same) and Cotton Cotyledon Box 6 had 53 samples analyzed and 1 call differed (98.1% same—see Table 6). The assay thus developed has been successfully used.

TABLE 6

Optimized TaqMan based PCR protocol for 384-well format for Cry1Ac detection.

| Component | Final Concentration | µl/Reaction |
|---|---|---|
| H$_2$O | | 7.01 |
| 10 X Buffer (15 mM MgCl$_2$) | 1 X | 1.00 |

TABLE 6-continued

Optimized TaqMan based PCR protocol for 384-well format for Cry1Ac detection.

| Component | Final Concentration | μl/Reaction |
|---|---|---|
| 10% PVP | 1 X | 1.00 |
| dNTP (10 mM) | 0.5 mM | 0.75 |
| MgCl$_2$ (25 mM)* | 2 mM | 1.20 |
| Common Event Primer (20 uM) 3006_WT_R9 SEQ ID NO: 2 | 0.2 uM | 0.15 |
| Transgene Forward Primer (20 uM) - 3006_WT_F9 SEQ ID NO: 3 | 0.2 uM | 0.15 |
| Transgene Probe (10 uM) 3006_IAC_Probe_8796 SEQ ID NO: 5 | 0.08 uM | 0.12 |
| Wild Type Forward Primer (20 uM) - 3006_WT_F6 SEQ ID NO: 4 | 0.4 uM | 0.30 |
| Wild Type Probe (10 uM) 3006_WT_P4 SEQ ID NO: 6 | 0.08 uM | 0.12 |
| Qiagen Taq Polymerase (5 U/μl) | 1 U/rxn | 0.20 |
| | Total Master Mix Volume | 12.00 |
| | Add 3 μl of DNA volume/reaction | 15 μl total |

*Total MgCl$_2$ = 3.5 Mm

Example 9

Conversion to 384 Well Format

The optimization of this assay required adjustments to both the MgCl$_2$ and the dNTP concentrations. The volume of PCR mix was reduced to 12 μl with 3 μl of DNA added to each well for a total volume of 15 μl per reaction.

The invention claimed is:

1. A method for determining event zygosity of a cotton plant comprising a 3006-210-23 event, said 3006-210-23 event comprising a transgene construct comprising a cry1Ac gene, said method comprising:
   obtaining a sample of genomic DNA from said cotton plant,
   contacting said sample with
      a. a first flanking primer consisting of SEQ ID NO:2;
      b. a second flanking primer consisting of SEQ ID NO:4;
      c. a transgene primer consisting of SEQ ID NO:3;
   wherein said first flanking primer and said second flanking primer form a wild-type amplicon when subjected to PCR conditions,
   wherein said transgene primer forms a transgene amplicon with said first flanking primer or said second flanking primer when subjected to PCR conditions,
   further contacting said sample with
      d. a florescent event probe that hybridizes with said transgene amplicon
      e. a florescent wild-type probe that hybridizes with said wild-type amplicon
   subjecting said sample to fluorescence-based endpoint TaqMan PCR conditions, quantitating said florescent event probe that hybridized to said event amplicon,
   quantitating said florescent wild-type probe that hybridized to said wild-type amplicon,
   comparing amounts of hybridized florescent event probe to hybridized florescent wild-type probe; and
   determining zygosity of said cotton tissue by comparing florescence ratios of hybridized fluorescent event probe and hybridized fluorescent wild-type probe.

2. The method of claim 1, wherein said plant comprises a first subgenome and a second subgenome, said transgene amplicon being formed from said first subgenome, and said wild-type amplicon being formed from said second subgenome.

3. The method of claim 1 wherein results of said method are read directly in a plate reader.

4. The method of claim 1 wherein said probes are labeled with a fluorescent dye and quencher.

5. The method of claim 1 wherein said transgene probe comprises TEXAS RED™ as said fluorescent dye at the 5' end of said transgene probe and BLACK HOLE QUENCHER (BHQ™) as said quencher on the 3' end of said transgene probe.

6. The method of claim 1 wherein said wild-type probe is labeled with a fluorescent dye (FAM) at the 5' end of said wild-type probe and a BLACK HOLE QUENCHER (BHQ™) as said at the 3' end of said wild-type probe.

7. The method of claim 1 wherein said wild-type probe comprises SEQ ID NO:6.

8. The method of claim 1 wherein said transgene probe comprises SEQ ID NO:5.

9. The method of claim 1 wherein said transgene amplicon comprises SEQ ID NO:8.

10. The method of claim 1 wherein said wild-type amplicon comprises SEQ ID NO:9.

* * * * *

SEQUENCE LISTING

```
<160> NUMBER OF SEQ ID NOS: 9

<210> SEQ ID NO 1
<211> LENGTH: 9382
<212> TYPE: DNA
<213> ORGANISM: Artificial Sequence
<220> FEATURE:
<223> OTHER INFORMATION: Cry1Ac Event 3006-210-23 including the insert
      and flanking sequences
<220> FEATURE:
<221> NAME/KEY: misc_feature
<222> LOCATION: (556)..(556)
<223> OTHER INFORMATION: n is a, c, g, or t

<400> SEQUENCE: 1
accaattatt atcgtctttt ttaattattc caacctttaa ctattatcct gccttaaaat      60
tcgaatacat ttattatcta taaactatcc gaatattatt atctaaatcc taattaaata     120 ctattttta tcgagtattc gtatccgcca aggaaatcca tctccaaatt ttcaattatt     180
tttcagatat ctaaatctgt aaaatttcaa attcaagtac gttacaattc tttataaata     240
atccaaatta taaatatttt ataactatta attcataaat taaaatttat tattcaaata     300
ttcgaataat ctatttttaa gacgtaaagt attacatcga agggttactt tcaaagggta     360
gtgtatttcc atttcaatta ttcagaacgt tgtcgttttg ttccggtcat agaaaagggc     420
tctggaagag aagaaaatga cttgactttt caatttcatg ctcatccact cgtttcaatt     480
actgtttact aaaaaaataa taaaataaaa tattaacaat gcattgagta tgatgtccgg     540
gaaatctaca tggatnagca atgagtatga tggtcaatat ggagaaaaag aaagagtaat     600
taccaatttt tttcaattc aaaaatgtag atgtccgcag cgttattata aaatgaaagt      660
acattttgat aaaacgacaa attcgatcc gtcgtattta taggcgaaag caataaacaa     720
attattctaa ttcggaaatc tttatttcga cgtgtctaca ttcacgtcca aatggggggcc     780 acttggctgc agccaagctt tcgcgagctc gagatccccg acatatgccc cggtttcgtt     840
gcgactaaca tgagttcttg gacaaatttg attggacctg atgagatgat ccaacccgag     900
gatatagcaa agctcgttcg tgcagcaatg gaacggccaa accgtgcttt tgtccccaag     960
aatgaggtgc tatgcatgaa ggaatctacc cgttgatgtc aacagtctc agggttaatg    1020
```

```
tctatgtatc ttaaataatg ttgtcggtat tttgtaatct catatagatt ttcactgtgc   1080
gacgcaaaaa tattaaataa atattattat tatctacgtt ttgattgaga tatctagatc   1140
tcgaggtgtg aagatatga attttttttga gaaactagat aagattaatg aatatcggtg   1200
ttttggtttt ttcttgtggc cgtctttgtt tatattgaga ttttttcaaat cagtgcgcaa   1260 gacgtgacgt aagtatccga gtcagttttt attttctac taatttggtc gtttatttcg    1320
gcgtgtagga catggcaacc gggcctgaat ttcgcgggta ttctgtttct attccaactt   1380
tttcttgatc cgcagccatt aacgactttt gaatagatac gtctagggtc gagggggat    1440 ccgtcgaggg ggtccaccaa aaacgtaagc gcttacgtac atggtcgagg ggtccacca    1500 aaaacgtaag cgcttacgta catggtcgag ggggtccacc aaaaacgtaa gcgcttacgt   1560
acatggtcga ggggtccac caaaaacgta agcgcttacg tacatggtcg actagagcgt   1620
gacgctcgcg gtgacgccat ttcgcctttt cagaaatgga taaatagcct tgcttcctat   1680
tatatcttcc caaattacca atacattaca ctagcatctg aatttcataa ccaatctcga   1740
tacaccaaat cgcggatccg tcgacctgca ggtcgacatg tctccggaga ggagaccagt   1800
tgagattagg ccagctacag cagctgatat ggccgcggtt tgtgatatcg ttaaccatta   1860
cattgagacg tctacagtga actttaggac agagccacaa acaccacaag agtggattga   1920
tgatctagag aggttgcaag atagataccc ttggttggtt gctgaggttg agggtgttgt   1980
ggctggtatt gcttacgctg ggccctggaa ggctaggaac gcttacgatt ggacagttga   2040
gagtactgtt tacgtgtcac ataggcatca aaggttgggc ctaggatcca cattgtacac   2100
acatttgctt aagtctatgg aggcgcaagg ttttaagtct gtggttgctg ttataggcct   2160
tccaaacgat ccatctgtta ggttgcatga ggctttggga tacacagccc ggggtacatt   2220
gcgcgcagct ggatacaagc atggtggatg gcatgatgtt ggttttttggc aaagggattt   2280 tgagttgcca gctcctccaa ggccagttag gccagttacc cagatctgag tcgacggatc   2340
cccgacatat gccccggttt cgttgcgact aacatgagtt cttggacaaa tttgattgga   2400
cctgatgaga tgatccaacc cgaggatata gcaaagctcg ttcgtgcagc aatggaacgg   2460
ccaaaccgtg cttttgtccc caagaatgag gtgctatgca tgaaggaatc tacccgttga   2520
tgtccaacag tctcagggtt aatgtctatg tatcttaaat aatgttgtcg gtattttgta   2580
atctcatata gattttcact gtgcgacgca aaaatattaa ataaatatta ttattatcta   2640
cgttttgatt gagatatcat caatattata ataaaaatat ccattaaaca cgatttgata   2700
caaatgacag tcaataatct gatttgaata tttattaatt gtaacgaatt acataaagat   2760
cgaatagaaa atactgcact gcaaatgaaa attaacacat actaataaat gcgtcaaata   2820
tctttgccaa gatcaagcgg agtgagggcc tcatatccgg tctcagttac aagcacggta   2880
tccccgaagc gcgctccacc aatgccctcg acatagatgc cgggctcgac gctgaggaca   2940
ttgcctacct tgagcatggt ctcagcgccg gctttaagct caatcccatc ccaatctgaa   3000
tatcctatcc cgcgcccagt ccggtgtaag aacgggtctg tccatccacc tctgtttggga  3060 attctgatct tggcgcgcat gcggatcctc attcctccat cagaagtaac tccacgctat   3120
caacaatgaa tgttccttcc gtttctccaa tctcaatcca aaccttgtcg gtttctggaa   3180
agtactctaa ctctttggtg acatagccgg ctggtaacgg tgtgtagtcc ccatagcctc   3240
tgttagattc gcaaggattg tccctacgtc catcggtgta agccttctcc tcataggctg   3300
atgcatagtc agcgggtaca gaagagttgc tctcataggc tccatcgtat cctcgattgc   3360
gagaagtgta agtaccctca tactcctctt gagtcgcagt gtagtcattg caagttacgg   3420
```

```
tgttgtttgg gtagacttcc tcctcgacgc agttgctgaa cttcagctcg tcggtgttgt   3480
tctcaatctc gtgtatggtg acgcaacctt ctccgtatcc ttctttgtac gcggtaacac   3540
gaagaatgta gccacgacca ggacagacac gaacttcttg tgaaacttct gcttcccact   3600
caggaacaac aaggacagag cggtgattgt tctgttcttc tacatctacg tgcccttcca   3660
cattccagca ggataggcca ttgttgaagt caccattctt gatgacattc ctcgcatcat   3720
acaaggagaa tgcagtgaag atgcgccctt ctaactcttc aaagatagca gcattgacac   3780
ccggaatcac gctaagttca ggaaggtaag cttcccgaat gctatgaacg cgtttgtctg   3840
cagcatgaat catagctatg ttggtatcag cttggagcct atcatactga gagttcacaa   3900
acagagcgtc aacgctttct ttggcttctt tgtacacaat gtttgtttcc cattccaact   3960
tctctctctt gtccctccac ttcttctcag ccctcttcac tctagcgagg gcttctccaa   4020
caagtggttt ctcttctaga aactccagat tgcctagcct ggcatggcca tcttgagtct   4080
tgatcttgaa gatcacccac acaccgaggt cttcgttcag gtcggtacag ccaacgtcta   4140
tgtccaagga gaagtggtgt gagtgatggg cacacttgcc gatgggactt ggggctgaaa   4200
gtggccagag tgaacccgtc ccaggcacat tgactgtctc atgtttggcg ttgtatctga   4260
tgaggtagat ctcaaggtct tgactgtcct cgatgtaacc tctcaactgg tatcttgtgt   4320
aggctttgag tttcgattca tctatcttct ggtacaggta tgttggatag cactcatcaa   4380
aggtacccaa gagcgtaaca tagttctcct tgaacacatc atcacctcct tgaatggtga   4440
tgtccgtact tcccctccat ccacgatcta gttgcctgtt gatcccgcga agttgggat    4500 cttgaagcaa gttccgctca tcactaagtc gcttagcatg tttgaccttc tcggacaact   4560
ccttcttctc atccaaacag aactcatcag agaggcactc aacaaggttg aaacgcgat    4620 cgatgtgata gtcagtcaca tctgtcttga gcccaatctg attggacgaa gtgaacagag   4680
cattcaccgc cttctgtgct ctttccaagt cagactctgc ctcgagcgtt gcagtaacgg   4740
gaatgaattc gaagcggtcg attatcactc cggcggttcc ggagaaattt ctaacaccta   4800
ctatgttacc tagggaagag gtgaaggcat tggcactttc gaagtaaccg aaatcgctag   4860
attggagatt atccaaggat gtagctgtcg ctggtactgt attggaaaag atggaggaat   4920 tacccccaatt gacgttgagg tgaataggg taacagaggc ataccttaca cgaacacgat   4980
atctggtaga tgtcgatggg aagtgaatgg gcacttcaat ataccctcta ttctggatgt   5040
tgttgccgga agaattcagc ctaaccaagt cgcctccagt gaatcctggt cctgaaatga   5100
cagaaccatt aaagagaaag ttccccttga cagctggat ctgagtaatg ctatcggatg    5160
caattatgtt gttaaactca gcactacgat gtatccaaga gaacatcgga gctctgatga   5220
tactaacgct gctattacta aagcctgaac ggaaacatgga cacatggcta aggcgatggc   5280
taaacccttg cctaggtgga acgttgttgt tctgtggagg gatctcatcc aagctatcaa   5340
ctgttccgct ctttctgtag acagcggatg gcagatttga ggaggttcca taggcaaatt   5400
ctgtcccgtc aagcacagac aattgttgat tgttgatgcc gatgttgaaa ggtctcctat   5460
atagagtgct ggacaaggtt ctatacacgc cctgaccgag ttgagcaaca atacgttgtt   5520
gtggagctgc attgcccata gtcccgtaaa gtggaaagt gaattctggt ccagagaacc    5580
caacgggtga tgccatgatc tgatgccctg accagtagta ataaccgcgg tgcgcatcgg   5640
tgtagatcgt gatactgttc aatatgtcca tcaggtgtgg agacctgatg cttctctcta   5700
tgccctgagc cgagcctcga aagctaccgt cgaagttctc gaggactggg tttgtgtaga   5760
```

```
tttcccgggt caattgtgac acagtacgga ttgggtagcg cctagagtcg tagttgggaa      5820
agagagcgac aatgtctagg acagttagtg tcaactctcg cctgaactgg ttgtacctga      5880
cccaatctct agaatccggt ccccagacac gttcgagacc cgtgttgtac cagcgaacag      5940
cataatcggt atagttgcca ataagcctag tcagatcatt ataacgacta ttgatagttg      6000
cggcatcaaa gccccaccgt tgtccgaaca cggagacatc gcggagcacc gacaagtgca      6060
ggttggcagc ctgcacgtac acggataaaa gaggaacttg gtaattctga acggcgaaga      6120
gcggaattgc ggtcgtcagc gcgctgttca tgtcattgaa ttgaatgcgc atctcctctc      6180
ttaaggcagg attggtcggg tctgcttccc actctcgaaa agattctgcg taaatctggt      6240
aaaggttgct gaggccttct aaccttgaga tggcttggtt cctagcgaat tcttctattc      6300
tttggttaat taactgctct atctgtacaa gaaaggcgtc ccattgagag ggaccaaaga      6360
ttccccaaat gatatcgaca agtccaagca cgaatccagc accgggcacg aactctgaca      6420
aaaggaattg ggtaagtgac aacgagatgt cgataggtgt gtaaccagtc tcaatccgtt      6480
ctccacccag cacctcaacc tcagggttgc tcaggcagtt gtaaggaatg cactcgttga      6540
tgttgggatt gttgtccatt gttggatcct ctagagtcga cctgcagaag taacaccaaa      6600
caacagggtg agcatcgaca aaagaaacag taccaagcaa ataaatagcg tatgaaggca      6660
gggctaaaaa aatccacata tagctgctgc atatgccatc atccaagtat atcaagatca      6720
aaataattat aaaacatact tgtttattat aatagatagg tactcaaggt tagagcatat      6780
gaatagatgc tgcatatgcc atcatgtata tgcatcagta aaacccacat caacatgtat      6840
acctatccta gatcgatatt tccatccatc ttaaactcgt aactatgaag atgtatgaca      6900
cacacataca gttccaaaat taataaatac accaggtagt ttgaaacagt attctactcc      6960
gatctagaac gaatgaacga ccgcccaacc acaccacatc atcacaacca agcgaacaaa      7020
aagcatctct gtatatgcat cagtaaaacc cgcatcaaca tgtataccta tcctagatcg      7080
atatttccat ccatcatctt caattcgtaa ctatgaatat gtatggcaca cacatacaga      7140
tccaaaatta ataaatccac caggtagttt gaaacagaat tctactccga tctagaacga      7200
ccgcccaacc agaccacatc atcacaacca agacaaaaaa aagcatgaaa agatgacccg      7260
acaaacaagt gcacggcata tattgaaata aaggaaaagg gcaaaccaaa ccctatgcaa      7320
cgaaacaaaa aaaatcatga aatcgatccc gtctgcggaa cggctagagc catcccagga      7380
ttccccaaag agaaacactg gcaagttagc aatcagaacg tgtctgacgt acaggtcgca      7440
tccgtgtacg aacgctagca gcacggatct aacacaaaca cggatctaac acaaacatga      7500
acagaagtag aactaccggg ccctaaccat ggaccggaac gccgatctag agaaggtaga      7560 gaggggggggg gggggaggac gagcggcgta ccttgaagcg gaggtgccga cgggtggatt      7620
tgggggagat ctggttgtgt gtgtgtgcgc tccgaacaac acgaggttgg ggaaagaggg      7680
tgtggagggg gtgtctattt attacggcgg gcgaggaagg gaaagcgaag gagcggtggg      7740
aaaggaatcc cccgtagctg ccggtgccgt gagaggagga ggaggccgcc tgccgtgccg      7800
gctcacgtct gccgctccgc cacgcaattt ctggatgccg acagcggagc aagtccaacg      7860
gtggagcgga actctcgaga ggggtccaga ggcagcgaca gagatgccgt gccgtctgct      7920
tcgcttggcc cgacgcgacg ctgctggttc gctggttggt gtccgttaga ctcgtcgacg      7980
gcgtttaaca ggctggcatt atctactcga aacaagaaaa atgtttcctt agttttttta      8040
atttcttaaa gggtatttgt ttaattttta gtcactttat tttattctat tttatatcta      8100
aattattaaa taaaaaaact aaaatagagt tttagttttc ttaatttaga ggctaaaata      8160
```

-continued

```
gaataaaata gatgtactaa aaaaattagt ctataaaaac cattaaccct aaaccctaaa    8220
tggatgtact aataaaatgg atgaagtatt atataggtga agctatttgc aaaaaaaaag    8280
gagaacacat gcacactaaa aagataaaac tgtagagtcc tgttgtcaaa atactcaatt    8340
gtcctttaga ccatgtctaa ctgttcattt atatgattct ctaaaacact gatattattg    8400
tagtactata gattatatta ttcgtagagt aaagtttaaa tatatgtata agatagata    8460 aactgcactt caaacaagtg tgacaaaaaa atatgtggt aatttttat aacttagaca    8520 tgcaatgctc attatctcta gagaggggca cgaccgggtc acgctgcact gcaggcatgc    8580
gcgccttaat taaggaattc ctcgagttta acggatccc tgaaagcgac gttggatgtt    8640
aacatctaca aattgccttt tcttatcgac catgtacgta agcgcttacg ttttggtgg    8700 accettgagg aaactggtag ctgttgtggg cctgtggtct caagatggat cattaatttc    8760
caccttcacc tacgatgggg ggcatcgcac cggtgagtaa tattgtacgg ctaagagcga    8820
atttggcctg tagacctcaa ttgcgagctt tctaatttca aactattcgg gcctaacttt    8880
tggtgtgatg atgctgactg gcttacgtgt ggaaaaaatt tgcaatctat gtagtcttta    8940
actaatgttt ttttctttaa aaaaaaagtc attattttg gtttgattaa tatatttggt    9000
ttaaattaaa taaaatatta aaaagtttag ttaaatcatc tatttaaacg atttgtactg    9060
atttgtgatc tattaatttt ttaacttaat ctagaccagg gtactagttg gtccgatccc    9120
atcttgaaaa cactatcttt agcttgctgg taggttccag ggtagaaggc agagactttt    9180
ttggagggtt tttattatta aatttatatt tttataattt ttaaatgatt aaaataaaaa    9240
tttattattt taagaggaga taaagtgcaa ttttaccata tattaattta aattttata    9300 aatttaaaaa agaaaaaaac taaaatttta attttatagg ttctaaaata ataaatataa    9360
cttactgagt tttttttaagc tt                                            9382
```

```
<210> SEQ ID NO 2
<211> LENGTH: 30
<212> TYPE: DNA
<213> ORGANISM: Artificial Sequence
<220> FEATURE:
<223> OTHER INFORMATION: Primer 3006_WT_R9

<400> SEQUENCE: 2
gataaatttg ctaaacatga ctaaacacta                                     30

<210> SEQ ID NO 3
<211> LENGTH: 25
<212> TYPE: DNA
<213> ORGANISM: Artificial Sequence
<220> FEATURE:
<223> OTHER INFORMATION: Primer 3006_WT_F9

<400> SEQUENCE: 3
atggatcatt aatttccacc ttcac                                          25

<210> SEQ ID NO 4
<211> LENGTH: 28
<212> TYPE: DNA
<213> ORGANISM: Artificial Sequence
<220> FEATURE:
<223> OTHER INFORMATION: Primer 3006_WT_F6

<400> SEQUENCE: 4
ttaagacgta aagtattaca tcgaaggg                                       28
```

```
<210> SEQ ID NO 5
<211> LENGTH: 28
<212> TYPE: DNA
<213> ORGANISM: Artificial Sequence
<220> FEATURE:
<223> OTHER INFORMATION: Probe 3006_IAC_Probe_8796

<400> SEQUENCE: 5
tattgtacgg ctaagagcga atttggcc                                          28

<210> SEQ ID NO 6
<211> LENGTH: 29
<212> TYPE: DNA
<213> ORGANISM: Artificial Sequence
<220> FEATURE:
<223> OTHER INFORMATION: Probe 3006_WT_P4

<400> SEQUENCE: 6
ttcaatttca tgctcatcca ctcgtttca                                         29

<210> SEQ ID NO 7
<211> LENGTH: 21
<212> TYPE: DNA
<213> ORGANISM: Artificial Sequence
<220> FEATURE:
<223> OTHER INFORMATION: Probe 3006_WT_P6

<400> SEQUENCE: 7
tcaattattc agaacgtttc c                                                 21

<210> SEQ ID NO 8
<211> LENGTH: 325
<212> TYPE: DNA
<213> ORGANISM: Artificial Sequence
<220> FEATURE:
<223> OTHER INFORMATION: Transgene amplicon produced with primers
      3006_WT_R9 (SEQ ID NO: 2) and 3006_WT_F9 (SEQ ID NO: 3)

<400> SEQUENCE: 8
atggatcatt aatttccacc ttcacctacg atgggggggca tcgcaccggt gagtaatatt      60
gtacggctaa gagcgaattt ggcctgtaga cctcaattgc gagctttcta atttcaaact     120
attcgggcct aacttttggt gtgatgatgc tgactggctt acgtgtggaa aaaatttgca     180
atctatgtag tctttaacta atgtttttttt ctttaaaaaa aaagtcatta tttttggttt    240
gattaatata tttggtttaa attaaataaa atattaaaaa gtttagttaa atcatctatt    300
taaacgattt gtactgattt gtgat                                           325

<210> SEQ ID NO 9
<211> LENGTH: 380
<212> TYPE: DNA
<213> ORGANISM: Artificial Sequence
<220> FEATURE:
<223> OTHER INFORMATION: Wild-type Amplicon produced with primers
      3006_WT_R9 (SEQ ID NO: 1) and 3006_WT_F6 (SEQ ID NO: 4)

<400> SEQUENCE: 9
ttaagacgta aagtattaca tcgaagggtt actttcaaag ggtagtgtat ttccatttca      60
attattcaga acgttgtcgt tttgttccgg tcatagaaaa gggctctgga agagaagaaa    120
atgacttgac ttttcaattt catgctcatc cactcgtttc aattactgtt tactaaaaaa    180
ataataaaat aaaatattaa caatgcattg agcttacgtg tggaaaaaat ttgcaatcta    240
tgtagtcttt aactaatgtt ttttttctta aaaaaaaagt cattattttt ggtttgatta    300
```

```
atatatttgg tttaaattaa ataaaatatt aaaaagttta gttaaatcat ctatttaaac    360
gatttgtact gatttgtgat                                                380
```